United States Patent [19]
Jimenez et al.

[11] Patent Number: 5,523,411
[45] Date of Patent: Jun. 4, 1996

[54] SYNTHESIS OF MITOMYCIN AND ITS ANALOGS

[75] Inventors: Leslie Jimenez; Zheng Wang, both of Piscataway, N.J.

[73] Assignee: Rutgers University, New Brunswick, N.J.

[21] Appl. No.: 212,889

[22] Filed: Mar. 14, 1994

[51] Int. Cl.$^6$ .................... C07D 487/02; C07D 487/14
[52] U.S. Cl. .................. 548/422; 548/421; 548/423; 548/428; 544/63; 544/72
[58] Field of Search ...................... 548/428, 422

[56] References Cited

U.S. PATENT DOCUMENTS

Re. 27,384   6/1972   Matui et al. ........................ 548/422

OTHER PUBLICATIONS

Basu et al. 1993. Biochemistry 32:4708–18.
Fukuyama and Yang. 1993. in *Studies in Natural Products Chemistry*. Atta–ur–rahman, ed. vol. 13. pp. 433–471.
Köhler et al. 1993. J. Org. Chem. 58:1680–86.
McClure and Danishefsky. (1993.) J. Am. Chem. Soc. 115:6094–6100.
Woo et al. 1993. J. Am. Chem. Soc. 115:1199–1200.
Dmitrienko et al. 1992. Tetrahedron Lett. 33:5705–08.
Fukuyama et al. 1992. J. Am. Chem Soc. 114:383–85.
McClure et al. 1991. J. Am. Chem. Soc. 113:8185–86.
McClure and Danishefsky. 1991. J. Org. Chem. 56:850–53.
Jones and Rapport. 1990. J. Org. Chem. 55:1144–46.
Cera et al. 1989. Biochemistry 28:5665–69.
Fukuyama and Goto. 1989. Tetrahedron Lett. 47:6491–94.
Terano et al. 1989. J. Antibiot. 42:145–48.
Yasuda and Williams. 1989. Tetrahedron Lett. 30:3397–3400.
Hirai et al. 1987. J. Antibiot. 40:607–11.
Iwami et al. 1987. J. Antibit. 40:589–93.
Kiyoto et al. 1987. J. Antibiot. 40:594–599.
Shimomura et al. 1987. J. Antibiot. 40:600–606.
Uchida et al. 1987. J. Am. Chem. Soc. 109:4108–09.
Tomasz et al. 1987. Science 235:1202–08.
Davis et al. 1986. J. Org. Chem. 51:4240–45.
Cory and Ritchie, 1983, S. Chem. Soc., Chem. Commun. 1016:1244–45.
Davis et al. 1980. J. Am. Chem. Soc. 102:2000–05.
Kishi. 1979. J. Nat. Prod. 42:549–68.
Tomasz and Lipman. 1979. J. Am. Chem. Soc. 101:6066–67.
Fukuyama et al. 1977. Tetrahedron Lett. 49:4295–98.
Nakatsubo et al. 1977. J. Am. Chem. Soc. 99:8115–16.
Nakatsubo et al. 1977. J. Am. Chem. Soc. 99:4835–36.
Leadbetter et al. 1974. J. Org. Chem. 39:3580–83.
Govindachari et al. 1965. Tetrahedron Lett. 21:2957–60.
Allen and Weiss. 1965. J. Org. Chem. 30:2904–10.
von E. Doering and Schreiber. 1955. J. Am. Chem. Soc. 77:514–520.

*Primary Examiner*—Mukund J. Shah
*Assistant Examiner*—Matthew V. Grumbling
*Attorney, Agent, or Firm*—Klauber & Jackson

[57] ABSTRACT

The present invention relates to the synthesis of mitomycin and analogs thereof that are useful as anticancer antibiotics. The invention further relates to analogs of mitomycin, which can be prepared according to the methods of synthesis provided. The synthetic method of the invention provides for reacting a derivitized indole with a dialkylvinylsulfonium salt to yield a tricyclic skeleton having the precursors of the fourth ring in one step, followed by an oxidation step or steps to close the fourth ring and prepare mitomycin or a related compound.

9 Claims, No Drawings

SYNTHESIS OF MITOMYCIN AND ITS ANALOGS

The research leading to the present invention was supported in part by a Biomedical Research Support Grant, Public Health Service Grant No. RR 07058-26. The government may have certain rights in the invention.

FIELD OF THE INVENTION

The present invention relates to the synthesis of mitomycin and analogs thereof that are useful as anticancer antibiotics. The invention further relates to analogs of mitomycin prepared using the method of synthesis provided herein.

BACKGROUND OF THE INVENTION

The natural product, mitomycin C, has proven to be a clinically useful antitumor agent (Carter and Crooke, 1979, *Mitomycin C Current Status and New Developments*, Academic Press: New York). Mitomycin C is not active in the quinone form and requires activation by either enzymatic or chemical reduction (Tomasz et al., 1987, Science 235:1204–8; Cera et al., 1989, Biochemistry 28:5665–69). Mild acidic treatment also results in alkylated mitosene derivatives (Tomasz and Lipman, 1979, J. Am. Chem. Soc. 101:6063–67). The activated mitomycin C undergoes loss of methanol and is capable of monofunctional and/or bifunctional covalent interaction with DNA (Tomasz et al, 1987, supra).

The discovery of mitomycin C has resulted in two total syntheses of this important natural product (Fukuyama et al., 1977, Tetrahedron Lett. pp. 4295–98; Nakatsubo et al., 1977, J. Am. Chem. Soc. 99:8115–16; Nakatsubo et al., 1977, J. Am. Chem. Soc. 99:4835–36; Kishi, 1979, J. Nat. Prod. 42:549–568) (Fukuyama et al., 1987, J. Am. Chem. Soc. 109:7881–82; Fukuyama and Yang, 1989, J. Am. Chem. Soc. 111:8303–4; Fukuyama and Yang, in *Studies in Natural Products Chemistry*, Atta-ur-Rahman (ed.), 1973, Elsevier Science Publishers B.V. 13:433–471). However, one of these methods for the total synthesis of mitomycin C requires 46 steps, with an overall yield of 0.2%. The second method requires 31 steps, with an overall yield of 6%.

Two new natural products related to mitomycin, FR900482 and FR66979, have recently been isolated from a *Streptomyces sandaensis* culture (Uchida et al., 1987, J. Am. Chem. Soc. 109:4108–9; Iwami et at., 1987, J. Antibiot. 40:589–593; Kiyoto et al., ibid, 594–599; Shimomura et at, ibid., 600–606; Hirai et at., ibid., 607–611; Terano et al., 1989, J. Antibiot. 42:145–148). These compounds (Woo et al, 1993, J. Am. Chem. Soc. 115:1199–1200) appear to be activated by either enzymatic or chemical reduction, and thus alkylate DNA in a manner like mitomycin C (Tomasz et al, 1987, supra; Tomasz and Lipman, 1979, supra; Basu et at., 1993, Biochemistry 32:4708–18),.

Mitomycin C causes severe delayed myelosuppression (i.e., it lowers the whim blood cell count), which has limited its clinical usefulness. Mitomycin C has the lowest redox potential of the naturally occurring mitomycins. As indicated above, reduction of the quinone form of mitomycin is necessary to the antibiotic properties of this drug. It is believed that an analog having a lower redox potential would exhibit greater alkylating efficiency, and thus be more therapeutically attractive. However, the synthesis and testing of such structural has been hindered by the lengthy, cumbersome and impractical synthetic strategies presently available.

For example, the novel structure and potential usefulness of FR900482 makes it an attractive synthetic target. However, as with mitomycin, there is no practical method to synthesize this drug: a 40-plus step total syntheses (Fukuyama et at., 1992, J. Am. Chem. Soc. 114:383–385), and several partial syntheses (Yasuda and Williams, 1989, Tetrahedron Lett. 30:3397–3400; Fukuyama and Goto, 1989, Tetrahedron Lett. 30:6491–94; Jones and Rapoport, 1990, J. Org. Chem. 55:1144–46; McClure and Danishefsky, 1991, J. Org. Chem. 56:850–53; McClure et at., 1991, J. Am. Chem. Soc. 113:8185–86; Dmitrienko et at., 1992, Tetrahedron Lett. 33:5705–8; McClure and Danishefsky, 1993, J. Am. Chem. Soc. 115:6094– 6100) of FR900482 have been reported.

Thus, them is a need in the art for a facile, efficient and economical method for the synthesis of tetracyclic mitomycin, including analogs and intermediates thereof.

There is a further need in the art for a facile, efficient and economical method for the synthesis of tetracyclic natural product analogs of mitomycin, including analogs and intermediates thereof.

There is yet a further need in the art to identify mitomycin analogs that demonstrate improved anticancer activity, decreased toxicity, or both.

These and other needs in the art are addressed by the present invention.

The citation of any reference herein is not an admission that such reference is available as prior art to the present invention.

SUMMARY OF THE INVENTION

Accordingly the present invention relates to process for the preparation of an intermediate useful in the preparation of mitomycin or a mitomycin-related compound. The process of the invention broadly comprises:

A. reacting a 2-formyl indole of the formula:

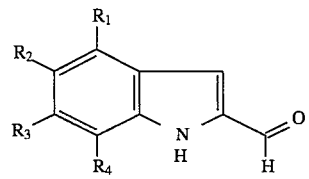

wherein $R_1$ or $R_4$ are independently selected from the group consisting of an amine, lower alkyl amine, hydroxy, lower alkoxy, or aryloxy, with the proviso that the group is non-reactive throughout the synthetic process, or wherein either $R_1$ or $R_4$, but not both, is H; and wherein $R_2$ and $R_3$ are independently a $C_1$ to $C_{10}$, preferably a $C_1$ to $C_4$, alkyl, alkenyl, alkynyl, heteroalkyl, heteroalkenyl, or heteroalkynyl group, or a $C_4$ to $C_{12}$ aryl or heteroaryl group;

with a dialkylvinylsulfonium salt having the formula:

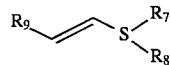

wherein $R_7$ and $R_8$ are each independently H; a $C_1$ to $C_{10}$ alkyl, alkenyl, alkynyl or aryl group; a $C_1$ to $C_{10}$ heteroalkyl, heteroalkenyl, heteroalkynyl or heteroaryl group; and wherein $R_9$ is H, a $C_1$ to $C_{10}$ alkyl, alkenyl, alkynyl, heteroalkyl, heteroalkenyl, or heteroalkynyl group, or a $C_4$ to $C_{12}$ aryl or heteroaryl group;

to form a product of the formula:

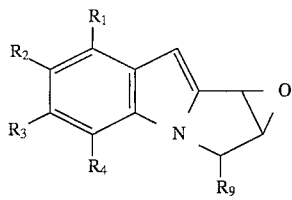

B. contacting the product of Formula (III) of step (a) with sodium azide to form an intermediate having the formula:

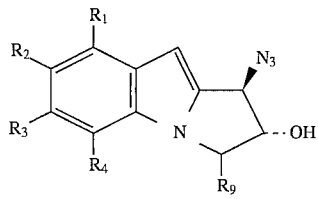

The process further comprises oxidizing the product of Formula (IV) step (b) to form an intermediate having the formula:

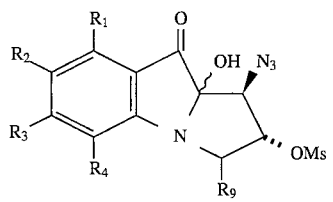

In a further aspect, the invention specifically relates to a strategy for the synthesis of a mitomycin-related compound, which further comprises the steps of:

c) acylating the product of the formula (IV) with an acylating agent $Cl_2CHOR_{10}$, in which $R_{10}$ is a $C_1$ to $C_{10}$ alkyl group, in the presence of $SNCl_4$ to form an intermediate of the formula:

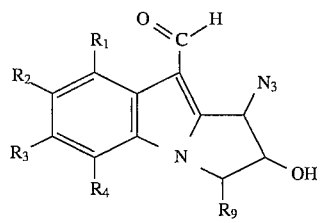

d) oxidizing the product of Formula (VII) under gentle conditions to form an intermediate of the formula:

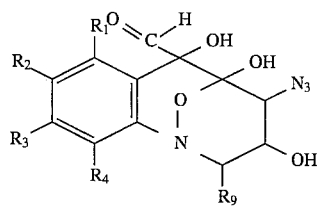

e) reducing the product of Formula (VIII) to yield a dialcohol, followed by reaction with diethyl azodicarboxylate (DEAD) to form a cyclopropyl epoxide intermediate product of the formula:

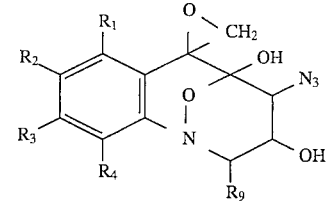

f) contacting the product of Formula (IX) with a Lewis acid, such as $FeCl_3$, opens the epoxide ring, to form an aldehyde, reducing the aldehyde to form an alcohol, and reacting the alcohol with phenylchloroformate, followed by bubbling with ammonia, to yield the carbamate of the formula:

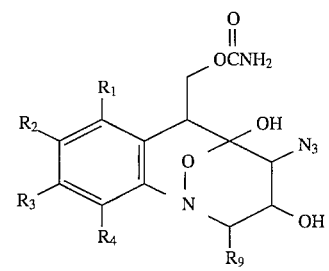

In yet a further embodiment, the invention relates to an alternative strategy for the synthesis of a mitomycin-related compound, which comprises the steps of:

c) introducing a protecting group on the ketone of the product of formula (V), to yield a product of the formula:

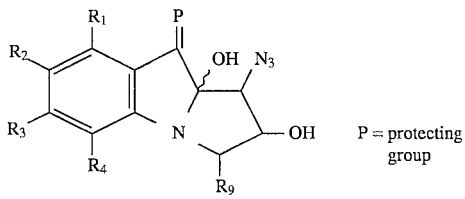

P = protecting group d) oxidizing the product of Formula (XI) under mild conditions, to yield a product of the formula:

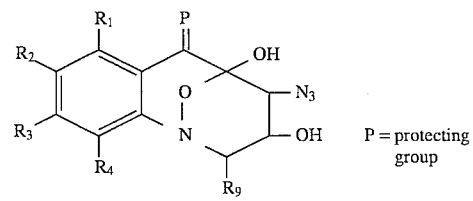

P = protecting group e) deprotecting the ketone group to yield a product of the formula:

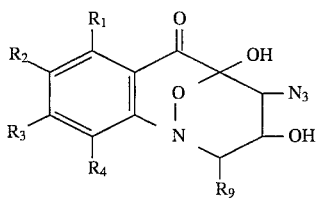

A final step of the process involves formation of a aziridine ring, which involves reacting the product of the terminal step with trialkylphosphine or triarylphosphine in the presence of a non-reactive base to form an aziridine ring.

The present invention further relates to the novel intermediates produced according to the present methods.

These and other aspects of the present invention will be better understood by reference to the following detailed description, Example, and Claims.

DETAILED DESCRIPTION OF THE INVENTION

The present invention relates to an efficient synthesis of tetracyclic mitomycin by reaction of a derivitized indole with a dialkylvinylsulfonium salt to yield a tricyclic skeleton having the precursor of the fourth ring in one step. Oxidation of this intermediate to form the mitomycin or mitomycin-related compound ring systems can be performed on one or three steps, respectively, followed by facile formation of the aziridine ring to complete the tetracyclic skeleton. The present invention accommodates modifications and variations known to those of skill in the art of the process for preparing the mitomycin or mitomycin-related compound skeleton in order to prepare derivatives and analogs of mitomycin or the mitomycin related compound, as described in detail herein.

Accordingly, various terms are used throughout this specification, which have the meanings given as follows:

The term mitomycin tetracyclic skeleton refers to compounds of the structure:

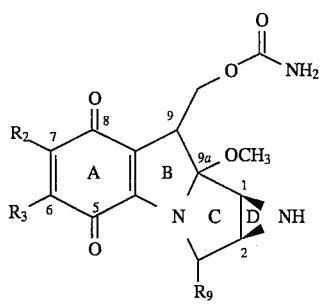

wherein the various R substituents are described above and infra. In specific embodiments, the invention contemplates preparation of the compounds mitomycin A and mitomycin C, which of the formulae:

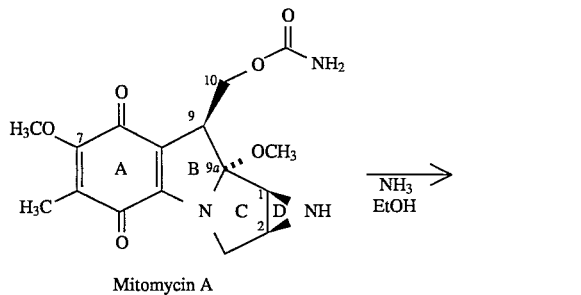

Mitomycin A

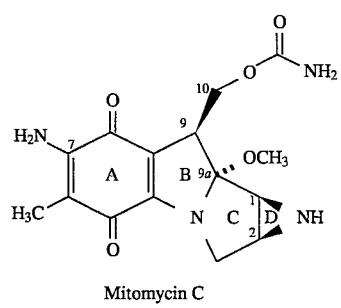

Mitomycin C

The term mitomycin-related compound tetracyclic skeleton refers to compounds of the structure:

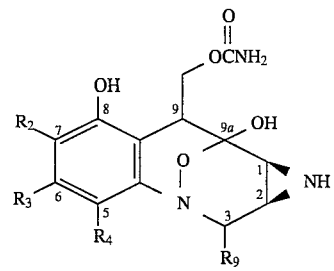

wherein the various R substituents are described above and infra. This skeleton differs from that of mitomycin by the presence of six membered rings B and C, which are formed by a N-O-C9 bond instead of an N-C9 bond, as found in the mitomycin skeleton. The term "mitomycin-related compound" is used herein to refer to the class of compounds similar in structure to FR900482 and FR66979, which have been isolated from *Streptomyces-sandaensis* culture, that have not to date received a generic name. The structure formulae of FR900482 and FR66979 are:

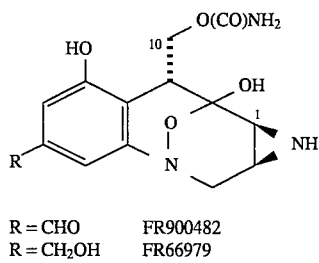

R = CHO      FR900482
R = CH$_2$OH      FR66979

The term "skeleton" is used herein to refer to the structure of compounds of the invention that is characteristic or each analog of the compound. Thus, the "skeleton" is the same regardless of the various substituents added to the compound.

Various functional groups can be attached to the skeleton to form mitomycin, mitomycin-related compound, or analogs thereof. The term "analog" refers to a functionally active form of the natural mitomycin or mitomycin-related compound. Throughout the specification and claims, such substituents are designated by the term "R" in the formula, and the following terms are used to define "R". Thus, as used herein, the term "alkyl" refers to a straight chain, branched chain, cyclic, or branched-cyclic hydrocarbon group, such as but not limited to, methyl, ethyl, propyl (including isopropyl), butyl (including isobutyl, tert-butyl, and cyclobutyl), pentyl (including cyclopentyl, as well as branched chain pentyl groups), hexyl (including cyclohexyl, as well as branched chain derivatives thereof), heptyl, octyl, nonyl and decyl, and the like. The term "alkenyl" refers to any of the foregoing alkyl groups having one or more unsaturated double bonds. The term "alkynyl" refers to any of the foregoing alkyl groups having one or more unsaturated triple bonds.

The term "aryl" refers to a conjugated system of pi electrons, in which there are an 4m+2 number of pi electrons (where m=an integer), with a minimum of six. Aryl groups include but are not limited to benzenes, pyridines, furans, pyroles and the like, including alkylated and heteroatom-substituted derivatives thereof. Heteroatom-containing aryl groups can have the heteroatom in the conjugated system, or as substituent groups.

The alkyl, alkenyl or alkynyl substituent groups can have from 1 to 10 carbon atoms ($C_1$ to $C_{10}$); preferably from 1 to 4 carbon atoms; and more preferably form 1 to 2 carbon atoms. The aryl substituent groups can have from 4 to 12 carbon atoms ($C_4$ to $C_{12}$).

As used herein, the term "hetero-" refers to a group as defined above having one or more heteroatoms, in particular, oxygen, nitrogen, or sulfur, in the group. When the heteroatom is oxygen, the group can be an alkoxy (including in which the oxygen is bonded to the skeleton), esther, ether, ketone, aldehyde, and the like. When the heteroatom is nitrogen, the group can be an amine (including in which the nitrogen is bonded to the skeleton), nitro group, hydrazide, hydrazine, hydrazone, and the like. When the heteroatom is sulfur, the group can be a sulfide, thioester, thioether, thiol, thioketone, thioaldehyde, and the like. Heteroatom containing substituent groups of the invention will generally include from 1 to 4 heteroatoms.

The term "intermediate" refers to a compound that is intended to undergo additional reactions in order to form a pharmaceutically active mitomycin (or analog thereof) or mitomycin-related compound (or analog thereof).

The term "pharmaceutically active" refers to the ability of a reduced form of a compound of the invention to alkylate a nucleophile.

As noted above, the present invention provides an efficient synthetic route for the preparation of compounds having the mitomycin tetracyclic skeleton or the mitomycin-related compound tetracyclic skeleton. In broad outline, the process of the invention comprises synthesis of a tricyclic intermediate, which can be used to prepare mitomycin or analogs thereof, or in two different strategies to prepare mitomycin-related compounds or analogs thereof.

Preparation of the Tricyclic Intermediate (a) Step (a) of the process reacts a substituted 2-formylindole group (I) with a dialkylvinylsulfonium salt (II) in the presence of strong base, such as hydride ion, e.g., sodium hydride, to form a 1,2-epoxy-2,3-dihydro-1-pyrrolo[1,2-a] indole (III). Generally, this reaction should proceed under anaerobic conditions, in an aprotic moderately polar solvent such as tetrahydrofuran (THF) at low temperature, preferably about 0° C. The reaction product may be purified, e.g., by recrystallization, washing, or flash chromatography, as desired.

(i) Substituted 2-formyl indole can be prepared by standard techniques (see, e.g., Remers et at., 1974, J. Org. Chem. 39:37580; Weiss et at., 1965, J. Org. Chem. 30:2897; Govindachari et at., 1965, Tetrahedron 21:2957–60). Since the C-3 carbon of indole is highly reactive, preferably substituted benzene is used to prepare the substituted indole. For example, benzene of the formula:

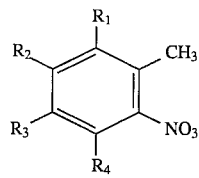

XIV in which either $R_1$ or $R_4$, or both, are selected from the group consisting of an amine, alkyl amine, hydroxy, alkoxy, or aryloxy, with the proviso that the group is non-reactive throughout the synthetic process, but can be oxidized to yield a quinone if the synthesis is of a mitomycin, or a hydroxy group at $R_1$ or $R_4$, preferably $R_1$, if the synthesis is of a mitomycin-related compound. In a preferred embodiment, $R_1$ is a selectively cleavable protecting group, such as the p-methoxy-benzoxy group of the formula:

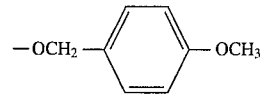

XV and $R_4$ is hydrogen. Use of a selectively cleavable protecting group provides prevents undesirable side reactions at $R_1$ (or, if desired, at $R_4$). Preferably, the selectively cleavable protecting group is resistant to mild oxidations, e.g., $MnO_2$ or Davis' reagent. At the end of the synthesis, the protecting group can be removed, yielding an oxidizable group in the case of mitomycin or analogs thereof, which upon oxidation forms a quinone. Alternatively, the protecting group can be removed to yield a hydroxyl group.

$R_2$ and $R_3$ can be independently a $C_1$ to $C_{10}$, preferably a $C_1$ to $C_4$, alkyl, alkenyl, alkynyl, heteroalkyl, heteroalkenyl, or heteroalkynyl group, or a $C_4$ to $C_{12}$ aryl or heteroaryl group. Preferably $R_2$ and $R_3$ are not aryl groups. In a specific embodiment, $R_2$ is all alkoxy group, in particular methoxy; or an alkyl amine group, in particular methyl amine; and $R_3$ is an alkyl group, in particular methyl; or hydrogen. In another specific embodiment, $R_3$ is an alkyl alcohol, in particular methanol (—$CH_2OH$); or an aldehyde, in particular formaldehyde (—CHO); and $R_2$ is and alkyl group, in particular methyl, or hydrogen.

The substituted benzene shown in (XIV) can be treated with a base, such as potassium butoxide or sodium hydride, and reacted with diethyloxylate in order to form the intermediate:

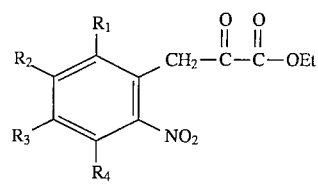

XVI

The nitro substituent of XVI is reduced, e.g., by treatment with Zn in hydrochloric acid (Zn-HCl), to yield the product of the formula:

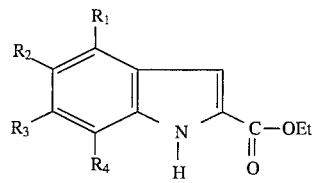

XVII

Reduction of the product XVII, e.g., with lithium aluminum hydride (LiAlH) or di-isopropyl alumina (DIBAL) yields the alcohol, which can be oxidized, e.g., with manganese dioxide ($MnO_2$) to form the substituted 2-formylindole (I). In a specific example, infra, the preparation of 2-formylindole from the starting material ethyl-2-indolecaxboxylate is described.

(ii) The dialkylvinylsulfonium salt can be prepared by reacting a 2-haloethylalkylsulfide, such as 2-chloroethylmethylsulfide, with an alkylhalide, such as iodomethane, to form 2-haloethyldialkylsulfonium halide, which is oxidized, e.g., with silver (I) oxide to form the dialkylvinylsulfonium salt. The 2-haloethylalkylsuflide can be substituted, e.g., with a $C_1$ to $C_{10}$, and preferably a $C_1$ to $C_4$, alkyl group. Generally the counterion of the salt will be a halide, such as $F^-$, $Cl^-$, $Br^-$ or $I^-$, but it could be any anion, e.g., an acid such as trifluoroacetate, and the like.

(b) Step (b) of the process then utilizes the resultant oxirane (III), which undergoes facile ring opening, with addition of sodium azide in an aqueous-organic solution, e.g., aqueous acetone, to yield the azido alcohol (IV).

Preferably, the azido alcohol is convened to the corresponding azido mesylate of the formula:

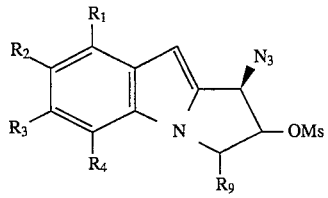

IVa by treatment with methanesulfonyl chloride (MsCl).

Intermediate (IV) or (IVa) can be further reacted using two strategies to prepare a mitomycin skeleton or a mitomycin-related compound skeleton. The strategy for preparing the mitomycin skeleton is taken first, followed by a strategy for the mitomycin-related skeleton.

Preparation of Mitomycin and Analogs Thereof (c) Oxidation of the azido alcohol or azido mesylate under gentle conditions in step (c) converts the indole to a hydroxy-pyrrole indole derivative (V). Preferably, the oxidation is performed with Davis' reagent (2-benzensulfonyl-3-phenyloxaziridine). This reaction can be performed in a protic solvent or solvent system, such as THF and water, preferably under an inert atmosphere.

This intermediate (V) can be used in a second strategy for preparing mitomycinrelated compounds, as described infra.

(d) Treatment of intermediate (V) with a trialkyl- or triarylphosphine, such as triphenylphosphine in the presence of a non-nucleophilic base, e.g., triethylamine, induces formation of the aziridine ring, yielding intermediate (VI). This reaction proceeds under similar conditions to the oxidation step (c).

(e) Three additional step are required to form pharmaceutically active mitomycin: the nitrogen of the aziridine ring must be protected, and the hydroxyl group acylated, e.g., with an acetyl group; the benzene structure of the indole group must be converted to the quinone or quinone precursor form; and the ketone group at C9 must be eliminated, preferably by replacing it with an appropriate leaving group, such as a carbamate. The manipulations required from this point on in the synthesis to yield mitomycin are well known in the art (e.g., Kishi, 1979, J. Nat. Prod. 42:549–568; see also Fukuyama et al., 1977, Tetrahedron Lett. pp. 4295–98; Nakatsubo et al, 1977, J. Am. Chem. Soc. 99:8115–16; Nakatsubo et al., 1977, J. Am. Chem. Soc. 99:4835–36).

Since the C9 ketone helps stabilize the nitrogen of the indole group, which is stabilized by the quinone of mitomycin. When the lone pair of electrons on nitrogen are not delocalized by either a quinone or the ketone, reformation of the C9-C9a double bond of the indole ting occurs. This event is necessary to the alkylating activity of mitomycin (i.e., after reduction of the quinone in vivo), but is not desirable prior to therapeutic use of the compound. Therefore, the present strategy seeks to maintain the stability of the indole nitrogen.

Accordingly, in a specific embodiment, formation of quinone follows reaction of the ketone of (VI) with Wittig reagent (alkylidene triphenylphosphorane) to form an extracyclic C—C double bond. Oxidation of the protected $R_1$ and/or $R_4$ positions of the benzene ring, e.g., by treatment with Fremy's salt (potassium dinitrosulfate), can then proceed, since otherwise the quinones would react with the Wittig reagent.

The methylene (exocyclic C—C double bond) is then treated to form an alcohol, e.g., by hydroboration. This alcohol is then easily converted to a carbamate by treatment with phenyl chloroformate, followed by bubbling with ammonia.

Subsequently, the protecting group on the aziridine ring can be removed, yielding a pharmaceutically active mitomycin or analog thereof, of the formula:

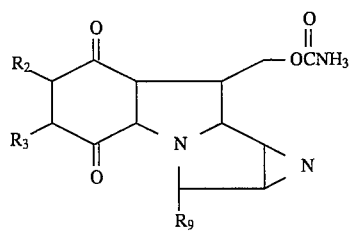

XVIII

Preparation of Mitomycin-Related Compounds—A (c) Intermediate (IV) is acylated by reaction with an acylating agent, such as $Cl_2CHOR_{10}$, in which $R_{10}$ is a $C_1$ to $C_{10}$, and preferably a $C_1$ to $C_4$, alkyl group, in the presence of $SNCl_4$ and in an appropriate solvent, e.g., $CH_2Cl_2$, to form an intermediate of the formula:

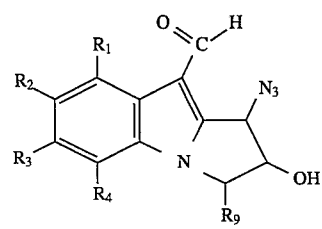

VII (d) In the next step, the intermediate (VII) is oxidized under gentle conditions, e.g., with Davis' reagent as described above, yielding intermediate of the formula:

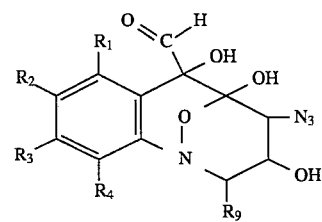

VIII (e) The substituents at C9 are treated to yield a carbamate leaving group. Intermediate (VIII) is reduced, e.g., by treatment with $NaBH_3$, to yield a dialcohol, followed by reaction with diethyl azoclicarboxylate (DEAD) to form a cyclopropyl epoxide intermediate (see McClure and Danishefsky, 1993, J. Am. Chem. Soc. 115:6094–6100) of the formula:

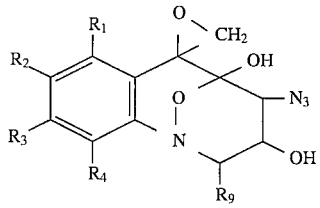

(f) Treatment of the intermediate (IX) with a Lewis acid, such as FeCl$_3$, opens the epoxide ring, yielding the aldehyde. The aldehyde can be reduced, e.g., by treatment with NaBH$_3$, to form the alcohol. The alcohol can be treated with phenylchloroformate, followed by bubbling with ammonia, to yield the carbamate of the formula:

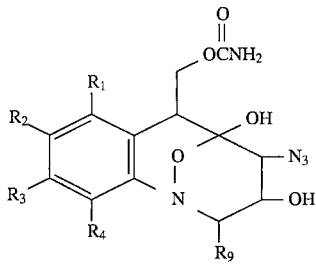

Synthesis of the mitomycin-related compound skeleton is then completed as described in step (d) of the synthesis of mitomycin and analogs thereof, supra, e.g., by treatment with a trialkyl- or triarylphosphine and non-nucleophilic base.

Preparation of Mitomycin-Related Compounds—B (d) It is believed that complete oxidation of intermediate (IV) can yield a bicyclic hemiacetal structure characteristic of the skeleton of the mitomycin-related compounds. However, the electron withdrawing ketone that forms at C9 prevents this complete oxidation reaction. Therefore protection of the ketone group should allow a second oxidation to yield the hemiacetal structure. Accordingly, intermediate (V), supra, is treated to block the ketone, resulting in an intermediate of the formula:

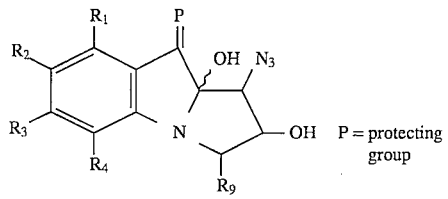

The protection of the ketone can proceed via one of three possible strategies:

(i) The ketone can be reacted with alcohol or a C$_2$ to C$_3$ diol to form an intermediate of the formula:

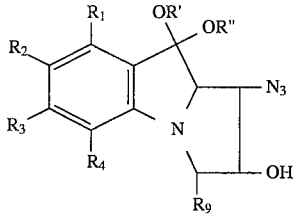

in which R' and R" can be a C$_1$ to C$_4$ alkoxy, or R' and R" together may be a lower alkyl bridge.

(ii) The ketone can be reacted with hydrazine to form a hydrazone of the formula:

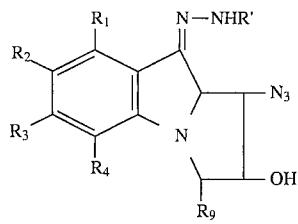

wherein R' can be a lower alkyl or hydrogen.

(iii) The ketone can be reacted with thiols, or a lower alkyl dithiol, to form the thioacetal of the formula:

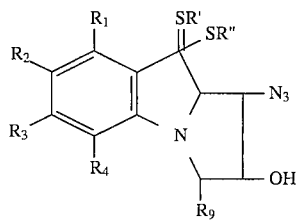

(e) The ketone protected intermediate (XI) can be treated with a mild oxidation reagent, such as Davis' reagent, to yield an intermediate of the formula:

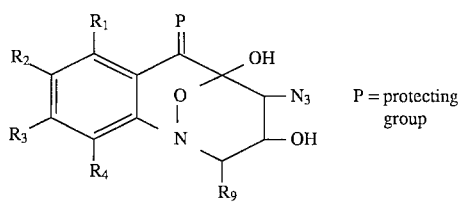

(f) The ketone group of intermediate (XII) is then deprotected. The acetal is deprotected by acidification; the hydrazone can be deprotected by treatment with a strong base (but the harsh reaction conditions are preferably avoided); the thioacetal can be deprotected by treatment with a Lewis acid, such as BF$_3$ or a mercuric halide. Deprotection of the ketone yields an intermediate of the formula:

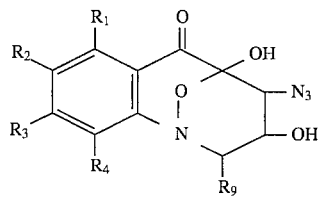

Synthesis of the mitomycin-related compound skeleton is then completed as described in step (d) of the synthesis of mitomycin and analogs thereof, supra, e.g., by treatment with a trialkyl- or triarylphosphine and non-nucleophilic base.

EXAMPLE

In a specific example, summarized in Scheme 1, 2-formylindole reacts with dimethylvinylsulfonium iodide (von Doering and Schreiber, 1955, J. Am. Chem. Soc. 77:514–520) or ethylmethylvinylsulfonium iodide in the presence of sodium hydride to give the tetracyclic oxirane 1. In this reaction, the vinylsulfonium salt presumably undergoes conjugate addition by the anionic indole to form the sulfur ylide in situ. The sulfur ylide then reacts at the carbonyl center to form an alkoxide, which displaces dimethylsulfide.

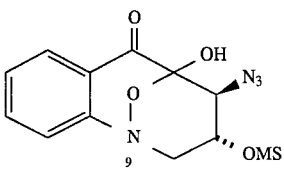

therefore, we initially believed we had formed compound 9, which possesses the FR900482 skeleton. This seemed to be in agreement with earlier results, in which a 2,3,9a- tetrahydro-9a-hydroxy-9-methoxy-9-methyl-1H-pyrrolo[1,2-a]indole was oxidized to the hydroxylamine hemiketal ring system of FR900482 with Davis' reagent (Dmitrienko et al., 1992, supra). Subsequently, a mass spectrum for 4 was obtained, which was consistent with the proposed structure of 4 in the Scheme.

Scheme 1

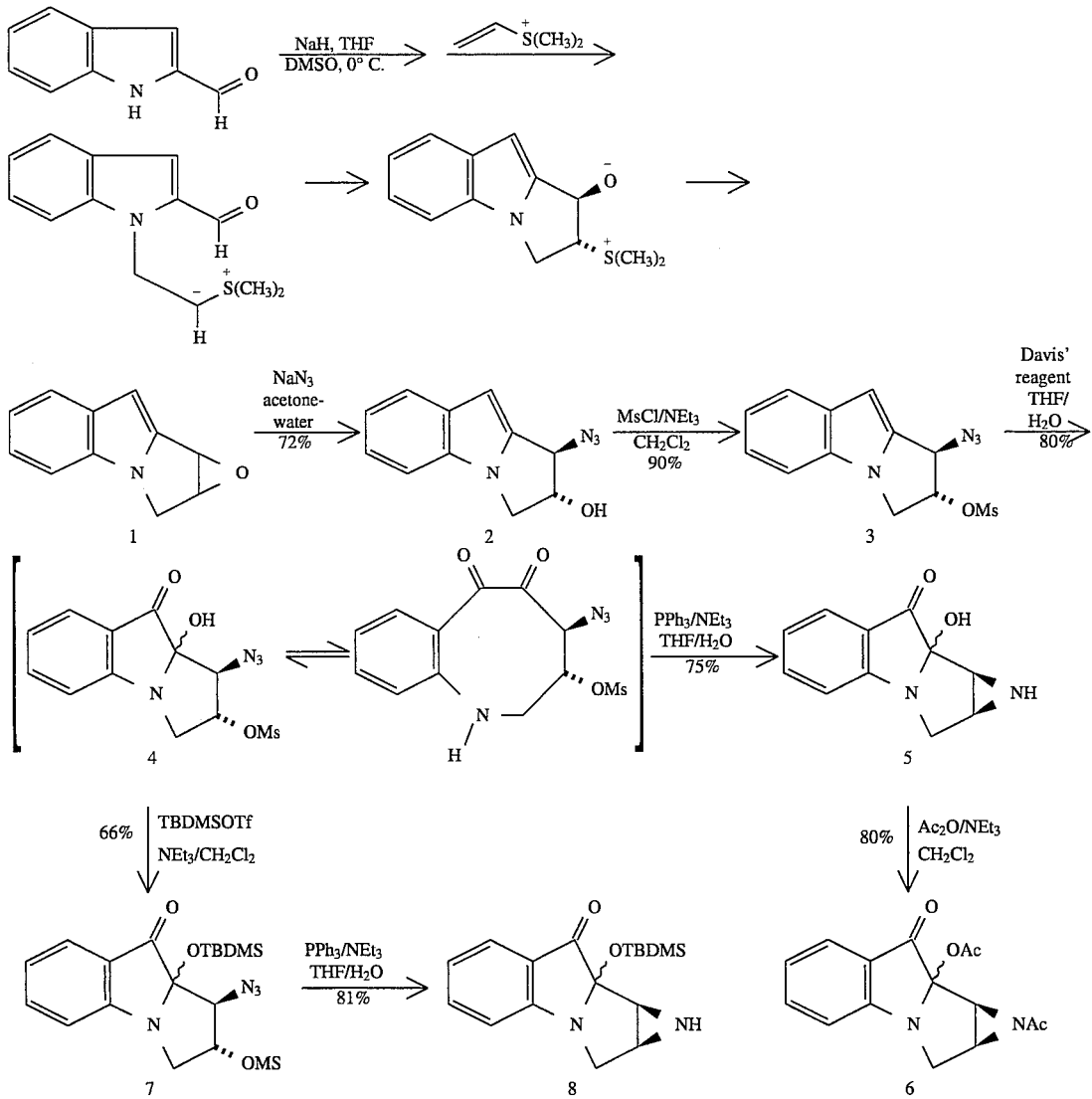

The oxirane is very prone to ring opening, thus our usual procedure is to add a solution of sodium azide in aqueous acetone to the oxirane and isolate the azido alcohol 2. This in turn was converted to the mesylate 3.

The mesylate undergoes oxidation upon treatment with 2-benzenesulfonyl-3-phenyloxaziridine (Davis' reagent) (Dmitrienko et al., 1992, Tetrahedron Lett. 33:5705–8; Davis et al., 1980, J. Am. Chem. Soc. 102:2000–5; Davis et al., 1986, J. Org. Chem. 51:4240–4245) to give 4. The azido mesylate 4 did not give a molecular ion in its mass spectrum, Treatment of 4 with triphenylphosphine in the presence of triethylamine (Fukuyama et al., 1992, J. Am. Chem. Soc. 114:383–385; Koehler et al., 1993, J. Org. Chem. 58: 1680–86) results in the formation of 5.

It was unclear whether triphenylphosphine reduces the hydroxylamine of the open keto form of 9, or whether 4 was the true intermediate. The two diastereomers of 4 can be separated by column chromatography, although they both reach an equilibrium of approximately 7:2 after 72 h in $CDCl_3$ as measured by $^1H$ NMR. t-Butyldimethylsilyl (TBDMS) group was introduced to the less stable of the two diastereomers to give a 66% yield of 7 as a 1:2 mixture of diastereomers. Apparently, some equilibration of the diastereomer of 4 takes place under the reaction conditions. An 81% yield of 8 was obtained from 7 as the same 1:2 mixture of diastereomers (7 cannot equilibrate), which indicates that 4 rather than 9 is the immediate precursor. The electron-withdrawing effect of the keto group apparently reduces the nucleophilicity of N-4, so that 4 rather than 9 is formed. Acetylation of 5 produces 6, which appears to exist as a single diastereomer by $^1$H and $^{13}$C NMR.

The advantage to this synthetic approach is that the third (c) ring and the precursor functional groups to the fourth (d) ring are formed in a single step. The oxidation with Davis' reagent gives the mitomycin ring system in another step, and the aziridine ring is formed easily in a third operation. Thus, the complete tetracyclic framework of mitomycin C is formed in four steps (overall yield=39%) from 2-formylindole.

Materials and Methods

2-Chloroethyldimethylsulfonium iodide:

A total of 2.6 g of 2-chloroethylmethylsulfide was dissolved in 10 mL of iodomethane and stirred at room temperature for 2 days. The crude product was filtered and washed by acetone (3×10 mL). 4.2 G of product were obtained after recrystalization from methanol (70%). $^1$H NMR (DMSO-d): $\delta$2.98 (s, 6H), 3.80 (t, 2H, J=12.8), 4.13 (t, H, J=12.8).

Dimethylvinylsulfonium iodide:

A solution of 3.9 g 2-chloroethyldimethylsulfonium iodide in 10 mL deionized water was stirred with 1.8 g of silver (I) oxide for 10 minutes. The mixture was filtered and the filtrate was acidified with acetic acid to pH 4, and then lyophilized to dryness. A total of 1.63 g of the product was obtained after recrystallization from ethanol-ether (49%). $^1$H NMR (DMSO-d$_6$): $\delta$3.15 (s, 6H), 6.50 (d, 1H, J=9.4), 6.56 (d, 1H, J=16.2).

2-Indolemethanol:

In a 50-mL round-bottom flask, a total of 2.28 g (12 mmol) of ethyl 2-indolecarboxylate was dissolved in 15 mL of dry THF under N$_2$. The solution was cooled to −78° C. (acetone-dry ice bath) and 24 mL (24 mmol) of 1.0M DIBAL in THF was added over a period of 1 h. The mixture was stirred for 2 h at −78° C., quenched with 10 mL of 1N HCl, then allowed to warm to room temperature. The reaction mixture was then extracted with ether (4×100 mL) and the ether layer was washed with 1N HCL (2×100 mL), dried over MgSO$_4$, filtered, and evaporated in vacuo. The product was purified by flash chromatography (1:1 ethyl acetate:petroleum ether). Yield: 1.76 g (99%). $^1$H NMR (CDCl$_3$): $\delta$1.86 (t, 1H, J=6, OH), 4.82 (d, 2H, J=6), 6.40 (s, 1H), 7.0–7.3 (m, 2H), 7.34 (d, 1H, J=7.8), 7.58 (d, 1H, J=7.8), 8.36 (br s, 1H) MS (EI): m/z 147 (M+).

2-Formylindole:

A total of 1.76 g of 2-indolemethanol was dissolved in dry CH$_2$Cl$_2$ (20 mL) at room temperature and stirred overnight with MnO$_2$ (2.1 g, 24 mmol). The mixture was filtered through Celite, the filtrate was evaporated under reduced pressure, and the product was purified by flash chromatography (CH$_2$Cl$_2$). Yield: 1.31 g (75%), $^1$H NMR (CDCl$_3$): $\delta$7.1–7.5 (m, 4H), 7.76 (d, 1H, J=7.8 Hz), 9.41 (br s, 1H), 9.86 (s, 1H).MS EI: m/z 145 (M+).

1,2-Epoxy-2,3-dihydro-1H-pyrrolo[1,2-a]indole (1):

In a 100-mL round-bottom flask, a total of 626 mg (4.31 mmol) of 2-formylindole and 259 mg (8.63 mmol) of NaH (80% dispersion in mineral oil) was stirred in 50 mL of dry THF under N$_2$ at 0° C. ice bath). A total of 935 mg (4.31 mmol) of dimethylvinylsulfonium iodide was added after 20 minutes and the reaction mixture was stirred overnight (about 15 hours). The mixture was then evaporated under reduced pressure and the residue was washed with pentane or hexane. The filtrate was evaporated under reduced pressure. The resulting solid was analyzed by GC-MS and had a purity of 99%. Yield: 665 mg (72%). $^1$H NMR (CDCl$_3$): $\delta$4.09 (dd, 1H, J$_1$=12), 4.33 (d, 1H, J=12), 4.40 (d, 1H, J=2.5), 4.50 (t, 1H, J=2.5), 6.59 (s, 1H), 0.0–7.3 (m, 3H), 7.60 (d, 1H, J=7.5), $^{13}$C NMR (CDCl$_3$: $\delta$45.94, 51.35, 60.83, 97.62, 109.23, 119.64, 121.68, 122.34, 131.44, 133.90, 139.12, MS (EI): m/z 171 (M+).

1-Azido-2,3-dihydro-2-hydroxy-1H-pyrrolo[1,2-a]indole (2):

In a 100-mL round-bottom flask, a total of 1.9 g (13 mmol) of 2-formylindole and 780 mg (26 mmol) of NaH (80% dispersion in mineral oil) was stirred in 150 mL of dry THF under N$_2$ at 0° C. (ice bath). At total of 3.39 g (15.7 mmol) of dimethylvinylsulfonium iodide was added after 20 minutes, and then the reaction mixture was stirred overnight (about 15 hours). A total of 3.38 g of NaN$_3$ (50 mmol) in 20 mL of 1:1 acetone:water was added to the reaction mixture, and then the reaction mixture was stirred at room temperature for about 12 hours. The mixture was evaporated under reduced pressure, and then purified by flash chromatography (3:2 petroleum ether:ethyl acetate). A yellow oil (2.0 g) was obtained (72%). $^1$H NMR (CDCl$_3$): $\delta$2.42 (d, 1H, J=5.5), 3.96 (dd, 1H, J=2.5, J$_2$=11), 4.39 (dd, 1H, J$_1$=5.5, J$_2$=11), 4.76 (m, 1H), 4.84 (br s, 1H), 6.56 (s, 1H), 7.10–7.39 (m, 3H), 7.65 (d, 1H, J=7.5). $^{13}$C NMR (CDCl$_3$ (CDCl$_3$): $\delta$50.2, 64.6, 79.8, 96.4, 109.7, 119.8, 121.5, 122.1, 131.9, 132.9, 137.1.

1-Azido-2,3-dihydro-2-methylsulfonyloxy-1H-pyrrolo[1,2-a]indole (3):

A total of 1.0 g of 2 (4.67 mmol) was dissolved in 10 mL dry CH$_2$Cl$_2$ at 0° C. Next, 1 mL of triethylamine was added, and then 1.45 mL (8 mmol) of methanensulfonyl chloride was added in small portions. The reaction mixture was stirred about 5 hours at room temperature (monitored by TLCO, and then 30 mL ether and 20 mL water were added. The phases were separated, and the organic layer was washed with 1N HCl (3×20 mL), 5% NaHCO$_3$ (3×20 mL), water (3×20 mL), and then dried over MgSo$_4$. After filtration, the solvent was removed under reduced pressure and the crude product was purified by flash chromatography (5:2 petroleum ether:ethyl acetate). Yield 1.22 g (90%). $^1$H NMR (CDCl$_3$): $\delta$3.13 (s, 3H), 4.32 (dd, J$_1$=2, J$_2$=12), 4.59 (dd, 1H, J$_1$=5.4, J$_2$=12), 5.21 (d, 1H, J=2), 5.5 (m, 1H), 6.60 (s, 1H), 7.1–7.3 (m, 3HO, 7.67 (d, 1H, J=8).

1-Azido-2,3-dihydro-8a-hydroxy-2-methylsulfonyloxy-8-oxo-1H-pyrrolo[1,2-a]indole (4):

A total of 480 mg of 3 (1.64 mmol) and 1.34 g of Davis' reagent (5.13 mmol) was stirred in 3 ml (THF/H$_2$O (10:1) under N$_2$ at room temperature for 14 hours. The mixture was evaporated under reduced pressure and the products (4a and 4b) were purified by flash chromatography (1:3 EtOAc:Petroleum ether). A total of 260 mg of 4a and 260 mg of 4b were obtained, which corresponds to an 80% conversion of 3 into 4. However, both diastereomers reached an equilibrium of approximately 7:2 4a:4b after 72 hours in CDCl$_3$ as measured by $^1$H NMR. For 4a: $^1$H NMR (CDCl$_3$): $\delta$1.7 (br, s, 1H), 3.0 (s, 3H), 3.37 (dd, 1H, J$_1$=6, J$_2$=11), 0.72 (d, 1H, J=8), 4.22 (dd, 1H, J$_1$=7, J$_2$=11), 5.4 (m, 1H), 6.8 (d, 1H, J=8), 7.0 (t, 1H, J=8), 7.6–7.7 (m, 2H). $^{13}$C NMR (CDCl$_3$): $\delta$38.20, 52.50, 64.90, 83.43, 93.04, 113.33, 120.02, 122.32, 125.68, 139.02, 162.14, 197.28. For 4b: $^1$H NMR (CDCl$_3$): δ1.9 (br s, 1H), 3.15 (s, 3H), 3.76 (dd, 1H, J$_1$=6, J$_2$=12), 3.96 (dd, 1H, J$_1$=3, J$_2$=12), 4.52 (m, 1H), 5.16 (m, 1H), 6.86 (d, 1H, J=8), 7.02 (t, J=8), 7.6 m, 2H). $^{13}$C NMR (CDCl$_3$): δ38.90, 54.65, 69.22, 82.73, 97.27, 113.18, 122.10, 122.36, 125.16, 138.68, 162.06, 196.93.

1, 1a, 2, 8a, 8b-Hexahydro-8a-hydroxy-8-oxoazirino[2',3':3,4]pyrrolo[1,2-a]indole (5):

A total of 120 mg of 4b (0.37 mmol), 200 mg of PPh$_3$, and 150 μΛ NEt$_3$ (1.08 mmol) was stirred in 3 ml THF/H$_2$O (10:1) under N$_2$ at room temperature for 3 hours. The mixture was evaporated under reduced pressure and the product was purified by flash chromatography (EtOAc). Yield: 56 mg (75%). The product appears as a single diastereomer in CDCl$_3$, but as two distinct diastereomers in acetone-d$_6$. $^1$H NMR (CDCl$_3$): δ37.37, 27.92, 51.73, 96.53, 113.12, 120.18, 122.84, 124.48, 138.10, 165.14, 199.92. Minor diasteromer: $^{13}$C NMR (Acetone-d$_6$) δ39.51, 40.14, 52.32, 96.66, 113.33, 120.18, 121.97, 124.28, 137.95, 164.41, 199.74, MS (EI 70 ev) m/z (M +) 202. MS (DCI) m/z (M+H+) 203.

1,1a,2,8,8a,8b-Hexahydro-8a-hydroxy-8-oxoazirino[2',3':3,4]pyrrolo[1,2-a]indole, monoacetate, monoacetamide (6):

A total of 30 mg (0.15 mmol) of 5, 70 μΛ of Ac$_2$O (0.75 mmol) and 105 μΛ of NEt$_3$ (0.75 mmol) was stirred in 1 mL dry CH$_2$Cl$_2$ under N$_2$ at room temperature overnight (~10 hours). The mixture was diluted with 10 mL CH$_2$Cl$_2$ and then washed with 3×15 mL saturated NaHCO$_3$, dried over sodium sulfate, filtered, and evaporated under reduced pressure. The product was purified by flash chromatography (1:1 CH$_2$Cl2:EtOAc). Yield: 34 mg (80%). $^1$H NMR (CDCl$_3$): δ1.95 (s, 3H), 2.13 (s, 3H0, 3.53 (d, 1H, J=12), 3.45 (d, 1H, J=12), 3.67 (m, 2H), 6.76 (d, 1H, J=8), 6.98 (t, 1H, J=7.5), 7.51 (t, 1H, J=8), 7.60 (d, 1H, J=7.5. $^{13}$C NMR (CDCl$_3$: δ20.56, 23.39, 41.94, 43.00, 51.76, 95.84, 11.55, 121.63, 122.82, 124.44, 137.57, 161.88, 168.43, 180.22, 193.95. MS (EI 70 ev) m/z (M+) 286.

1-Azido-2,3-dihydro-8a-(1,1-dimethylethyl)dimethylsilyloxy-2-methylsulfonyloxy-8-oxo-1H-pyrrolo[1,2-a]indole (7):

A total of 80 mg of 4b (0.24 mmol), 200 μΛ of t-butyldimethylsilyl trifluoromethanesulfonate (0.87 mmol), and 250 μΛ of Net$_3$ (1.8 mmol) was stirred in 3 mL dry CH$_2$Cl$_2$ under N$_2$ at room temperature for 4 hours. The mixture was diluted with 10 mL Ch$_2$Cl$_2$, and washed with 3×10 mL of H$_2$O. The organic phase was dried over sodium sulfate, filtered, evaporated under reduced pressure, and the two diastereomers were purified as a mixture by flash chromatography (2:1 Ch$_2$Cl$_2$:Petroleum ether). Yield: 70 mg (66%). An $^1$H NMR spectrum of the mixture in CDCl$_3$ revealed a 1:2 ratio of 7a:7b. 7a: $_1$H NMR (CDCl$_3$): δ091 (s, 9H), 0.95 (s, 6H), 3.09 (s, 3H), 3.42 (dd, 1H, J$_1$=6, J$_2$=12), 3.43 (d, 1H, J=7), 4.12 (dd, 1H, J$_1$=7, J$_2$=12), 5.38 (m, 1H), 6.87 (d, 1H, J=8), 7.05 (t, 1H, J=7), 7.5–7.7 (m, 2H). 7b: $_1$H NMR (CDCl$_3$): δ0.91 (s, 9H), 0.95 (s, 6H), 3.12 (s, 3H), 3.83 (dd, 1H, J$_1$=6, J$_2$=12.8), 3.88 (dd, 1H, J$_1$=3, J$_2$=12.8), 4.40 (d, 1H, J=2), 5.16 (m, 1H), 6.84 (d, 1H, J=7.8), 7.03 (t, 1H, J=7.4), 7.5–7.7 (m, 2H).

1,1a,2,8,8a,8b-Hexahydro-8a-(1,1-dimethylethyl)dimethylsilyloxy-8-oxoazirino[2',3':3,4]pyrrolo[1,2-a]indole (8):

A total of 70 mg of 7 (0.15 mmol), 60 mg of PPh$_3$ (0.22 mmol), and 63 μΛ of NE$_3$ (0.45 mmol) was stirred in 2 mL THF/H$_2$O (10:1) under N$_2$ at room temperature for 2 hours. The mixture was evaporated under reduced pressure and the product (a mixture of the two diastereomers) was purified by flash chromatography (1:1 CH$_2$Cl$_2$:EtOAc). Yield: 41 mg (81%). $^1$H NMR (CDCl$_3$): δ0.89 (s, 9H), 0.92 (s, 6H), 3.03 (m, 1H), 3.50 (m, 2H), 3.82 (d, 1H, J=12.5), 4.29 (m, 1H), 6.87 (d, 1H, J=8), 7.03 (t, 1H, J=7.5), 7.5–7.7 (M, 2H). MS (EI 70 ev) 316 (M+). MS (DCI): m/z 317 (M+H+).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A process for the preparation of a compound of formula IV useful in the preparation of mitomycin or a mitomycin-related compound comprising the steps of:

a) reacting a 2-formyl indole of the formula:

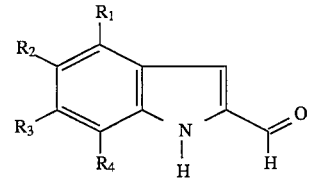

wherein R$_1$ and R$_4$ are independently selected from the group consisting of a C$_1$ to C$_{10}$ amine, alkyl amine, hydroxy, alkoxy, or aryloxy, with the proviso that the group is non-reactive throughout the synthetic process, or wherein either R$_1$ or R$_4$, but not both, is H; and wherein R$_2$ and R$_3$ are independently a C$_1$ to C$_{10}$ alkyl, alkenyl, alkynyl, heteroalkyl, heteroalkenyl, or heteroalkynyl group, or a C$_4$ to C$_{12}$ aryl or heteroaryl group;

with a dialkylvinylsulfonium salt having the formula:

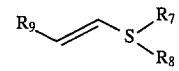

wherein R$_7$ and R$_8$ are each independently H; a C$_1$ to C$_{10}$ alkyl, alkenyl, alkynyl or aryl group; a C$_1$ to C$_{10}$ heteroalkyl, heteroalkenyl, heteroalkynyl or heteroaryl group;

and wherein R$_9$ is H, a C$_1$ to C$_{10}$ alkyl, alkenyl, alkynyl, heteroalkyl, heteroalkenyl, or heteroalkynyl group, or a C$_4$ to C$_{12}$ aryl or heteroaryl group;

to form a product of the formula:

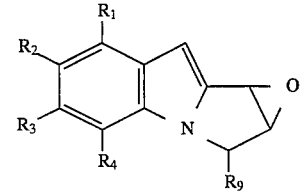

b) contacting the product of Formula (III) of step (a) with sodium azide to form an intermediate having the formula:

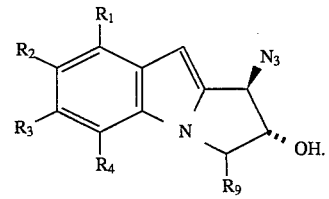

2. The process according to claim 1, further comprising oxidizing the product of Formula (IV) step (b) to form an intermediate having the formula:

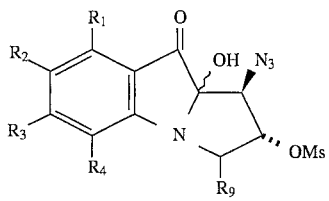
IVb

3. The process according to claim 1, further comprising reacting the product of the terminal step with trialkylphosphine or triarylphosphine in the presence of a non-reactive base to form an aziridine ring.

4. The method according to claim 2 comprising reacting the azido alcohol with methanesulfonyl chloride to form the azido mesylate prior to oxidizing the product of Formula (IV).

5. An intermediate of the formula:

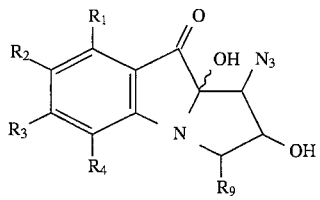
V wherein $R_1$ and $R_4$ are independently selected from the group consisting of a $C_1$ to $C_{10}$ amine, alkyl amine, hydroxy, alkoxy, or aryloxy, with the proviso that the group is non-reactive throughout the synthetic process, or wherein either $R_1$ or $R_4$, but not both, is H; wherein $R_2$ and $R_3$ are independently a $C_1$ to $C_{10}$ alkyl, alkenyl, alkynyl, heteroalkyl, heteroalkenyl, or heteroalkynyl group, or a $C_4$ to $C_{12}$ aryl or heteroaryl group; and wherein $R_9$ is H, a $C_1$ to $C_{10}$ alkyl, alkenyl, alkynyl, heteroalkyl, heteroalkenyl, or heteroalkynyl group, or a $C_4$ to $C_{12}$ aryl or heteroaryl group.

6. An intermediate of the formula:

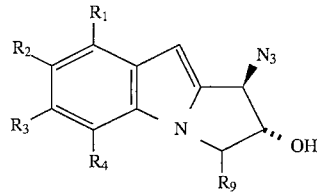
IV wherein $R_1$ and $R_4$ are independently selected from the group consisting of a $C_1$ to $C_{10}$ amine, alkyl amine, hydroxy, alkoxy, or aryloxy, with the proviso that the group is non-reactive throughout the synthetic process, or wherein either $R_1$ or $R_4$, but not both, is H; wherein $R_2$ and $R_3$ are independently a $C_1$ to $C_{10}$ alkyl, alkenyl, alkynyl, heteroalkyl, heteroalkenyl, or heteroalkynyl group, or a $C_4$ to $C_{12}$ aryl or heteroaryl group; and wherein $R_9$ is H, a $C_1$ to $C_{10}$ alkyl, alkenyl, alkynyl, heteroalkyl, heteroalkenyl, or heteroalkynyl group, or a $C_4$ to $C_{12}$ aryl or heteroaryl group.

7. The method according to claim 1, wherein $R_2$ and $R_3$ are a $C_1$ to $C_4$ alkyl, alkenyl, alkynyl, heteroalkyl, heteroalkenyl, or heteroalkynyl group.

8. The intermediate of claim 5, wherein $R_2$ and $R_3$ are a $C_1$ to $C_4$ alkyl, alkenyl, alkynyl, heteroalkyl, heteroalkenyl, or heteroalkynyl group.

9. The intermediate of claim 6, wherein $R_2$ and $R_3$ are a $C_1$ to $C_4$ alkyl, alkenyl, alkynyl, heteroalkyl, heteroalkenyl, or heteroalkynyl group.

* * * * *